United States Patent [19]

House

[11] 4,011,264

[45] Mar. 8, 1977

[54] CARBOXYMETHYLOXYSUCCINATES

[75] Inventor: Ralph House, El Sobrante, Calif.

[73] Assignee: Chevron Research Company, San Francisco, Calif.

[22] Filed: Dec. 20, 1974

[21] Appl. No.: 534,999

[52] U.S. Cl. .................. 260/535 P; 252/89 R; 252/132; 252/135; 252/182; 252/539; 252/DIG. 11; 260/484 P

[51] Int. Cl.$^2$ ............................. C07C 59/12

[58] Field of Search ..................... 260/535 P

[56] References Cited

UNITED STATES PATENTS 3,293,176  12/1966  While ................. 260/535 P

Primary Examiner—Paul J. Killos
Attorney, Agent, or Firm—G. F. Magdeburger; John Stoner, Jr.; W. Keith Turner

[57] ABSTRACT

Carboxymethyloxysuccinate derivatives are new compounds whose water-soluble salts are effective sequestering agents (builders), especially in heavy-duty laundering compositions. The salts may be used in combination with anionic, nonionic, ampholytic and zwitterionic detergents. A process for the preparation of the acids and salts is provided.

5 Claims, No Drawings

CARBOXYMETHYLOXYSUCCINATES

BACKGROUND OF THE INVENTION

1. Field of the Invention

This invention is concerned with novel builder materials and detergent compositions containing builder materials which provide good heavy-duty detergency in combination with conventional detergent actives.

The function of a "builder" in detergent compositions has not been in the past clearly defined except in terms of the enhancement of detergent activity of soaps and detergents when builders are employed in combination. It, however, is known that the presence of builders particularly enhances detergency when the detergent compositions are employed in hard water, so it has been conjectured that some large amount of the effectiveness of the builder results from the ability to tie up the so-called "hardness ions" in the water, i.e., calcium and magnesium ions. Builders have been therefore regularly employed in washing compositions designed for use in heavy-duty applications—that is, cleansing of washable fabrics, particularly cotton, in powered washing machines.

Increased concern over water pollution has caused a great demand for substitutes for the components of conventional heavy-duty detergent compositions. Thus branched-chain alkylbenzene sulfonates, which were used for many years as the active components of most heavy-duty detergent compositions, have been replaced in the United States as well as many foreign countries with linear alkylbenzene sulfonates, which possess the advantage of being biodegradable and thus do not contribute to the foam situation which had begun to become serious in rivers, streams and lakes.

A more recent, and one believed by many to be a more significant problem, lies in the phenomenon of eutrophication, which has contributed to the destruction of water bodies. This phenomenon, which involves the greatly increased growth of algae in the water bodies, results in removal of dissolved oxygen from the water bodies resulting in eventual death of almost all present living organisms. It is believed by many, and increasing evidence appears to indicate, that the presence of phosphates, largely derived from heavy-duty detergents, accounts for eutrophication.

Attempts to eliminate the phosphate builders have been made using one of two approaches. First, efforts have been made to provide new detergent-active materials which do not require the presence of any builder for heavy-duty washing, and secondly, efforts have been made to simply replace the phosphate builders with builder materials which lack the nutrient potential of phosphate. The second approach has resulted in the introduction of various materials as builders none of which has been completely successful in replacing phosphates because of other problems encountered. For example, the salts of nitrogen-containing polycarboxylic acids have been proposed, the most widely used—the polysodium salt of nitrilotriacetic acid—encountering extreme difficulty from findings that this compound, when in the presence of certain heavy metals, possesses possibly dangerous teratogenic activity. Other materials, such as various metal carbonates and silicates, etc., have been used but have been found to leave substantial deposits on clothes and in many cases are dangerously corrosive to human skin. Polyelectrolyte builders such as copolymers of ethylene and maleic acid are beleieved to be incapable of bacterial degradation and thus possess some disadvantages in use. Sodium citrate is used in some heavy-duty liquid detergents, its usefulness being limited from economic considerations.

SUMMARY OF THE INVENTION

It has now been found that compounds of the following formula are effective builders in detergent formulations:

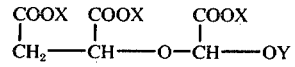

wherein Y is H or

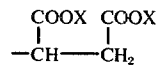

and X is H or a water-soluble salt-forming cation.

The compounds are prepared by reacting an appropriate quantity (from 1 to 2 mols of maleic anhydride with 1 mol of glyoxylic acid and neutralizing the product with an appropriate base.

The product, depending upon the amount of maleic anhydride employed, will be either a carboxyhydroxymethyl oxysuccinate or carboxymethyl bisoxysuccinate. Usually a mixture of the compounds will be produced, although careful control of the reactant ratios will produce a large predominance of one or the other compound.

The reaction is carried out at a temperature in the range about 20° to 120° C, preferably from about 50° to 100° C.

The heavy-duty detergent compositions in which the builders are useful comprise (1) an organic water-soluble anionic, nonionic, ampholytic or zwitterionic detergent-active material and (2) as a nonpolluting builder in an amount sufficient to enhance the detergency of the composition, carboxyhydroxymethyloxysuccinate, carboxymethylbisoxysuccinate or combinations thereof.

The formulations may be employed in which the builder is used in combination with any conventional heavy-duty detergent active. These materials, of course, incldude anionic, ampholytic, zwitterionic, and nonionic materials.

The most useful class of anionic materials which are included in the compositions are the alkyl aryl sulfonates, particularly the straight chain materials, which are usually nonsulfonates of alkylbenzene in which the alkyl chain contains from about 10 to 15 carbon atoms. These materials which are known as linear alkylbenzene sulfonates (LAS) have in recent years accounted for the bulk of heavy-duty detergent materials. These materials are prepared by reacting $C_{10}$ to $C_{15}$ olefins with benzene followed by sulfonation.

The anionic materials which may be used include soaps, not strictly detergents, which are the salts, usually the sodium, potassium, ammonium, etc., salts of higher fatty acids. Another representative class of suitable anionic detergents are the olefin sulfonates which are produced by the sulfonation of olefins generally of about 10 to 24 carbon atoms with sulfur trioxide followed by hydrolysis and neutralization of the reaction mixture. Another class of suitable anionic materials are those produced by the hydrogenation of the olefin sulfonates to the extent that at least 50 % of the ethylenic double bonds in the mixture are hydrogenated.

Examples of the nonionic materials include various ethoxylated or polyethoxy compounds which may be prepared by treating an alcohol, a phenol, or a carboxy acid with ethylene oxide. The most widely used of these materials are the condensation products of long chain alcohols with ethylene oxide—for example, the product obtained by condensing from 6 to 20 or more mols of ethylene oxide with n-dodecanol. Particularly useful materials are the polyethyoxy derivatives of straight chain primary alcohols of 10 to 18 carbons in which about 5 to 30 ethyleneoxy groups are present. The polyethoxy esters are exemplified by those compounds made by condensing ethylene oxide with oxidized paraffin wax. Other materials which have been oxylated to form nonionic surface-active esters include alkyl cyclohexene carboxylic acids, rosin acids, acids, of various modified rosins, and long-chain ethyl ethers of thioglycolic acid.

Another class of suitable nonionic surfactants are the polyhydroxy derivatives such as those produced by esterification of sugar alcohols such as sorbitol and mannitol. Similar materials may be prepared from the glucose derivatives including the fatty acid esters of hydroxypropyl glucoside.

Suitable zwitterionic detergent actives are derived for aliphatic quaternary ammonium compounds having straight- or branched-chain aliphatic radicals, at least one of which contains about 8 to 20 carbon atoms and also contains an anionic hydrophyllic group such as a sulfate or sulfonate group, etc.

The ampholytic surfactants which may be included in the composition are those materials which contain both acidic and basic functions in their structures. Examples of these materials include compounds having either carboxy or phosphoric esters as the acidic group and non-quanternary nitrogen as the basic group. Another example of a typical ampholytic detergent-active material is the water-soluble salt of dodecylbeta-alanine.

The concentration of surface-active material in the detergent formulations will generally be from about 10 to 30%, preferably 15 to 25% by weight. The ratio of the builder material to the detergent-active will generally be in the range of from about 8:1 to 1:8, preferably 5:1 to 1:5.

The formulations may be employed in dry form as either powdered or granulated materials or as liquid materials.

In addition to the detergent-active materials and builder of the composition there may be optionally present additional ingredients which enhance the detergent properties of the composition. Such materials may include but are not limited to anticorrosion, antiredeposition, bleaching, and sequestering agents, as well as various filler materials such as the inorganic alkali metal and alkaline earth metal salts such as the sulfates, carbonates, silicates or borates, etc. Typically, sodium sulfate will be present in the compositions because it is in many cases, and particularly with sulfuric acid-derived anionic actives, a by-product of the detergent preparation.

The cations which may be employed with the anionic detergent-active materials as well as those cations which are employed in conjunction with the builder material (as X in the formula) are, as previously noted, water-soluble, salt-forming materials. Representative of these cations are those of the alkali metals and ammonium. The alkali metal cations are preferred, and particularly preferred is sodium.

The following examples illustrate the preparation and testing of the compositions of this invention. The examples are illustrative and non-limiting.

EXAMPLES

EXAMPLE 1

Maleic anhydride (MA) and glyoxylic acid hydrate (GOAH) were dissolved in about 10 times their combined weight of water and stirred for 10 minutes to assure hydrolysis of MA. An excess of $Ca(OH)_2$ was then added in increments while stirring vigorously and the resulting mixture was refluxed with stirring for the designated time. $Na_2CO_3$ in excess of the $Ca(OH)_2$ was then added with stirring and stirred for 10 minutes more. The $CaCO_3$ formed was then filtered off and washed with hot water to recover all of the product as the sodium salt. Analyses were obtained by evaporating a weighed fraction of the total final solution, dissolving the residue in $D_2O$, running a nuclear magnetic resonance (NMR) spectrum, and comparing the unconverted MA and fumaric acid at about 6.0 and 6.5 ppm respectively and the product doublet at about 2.6 ppm using ethylene glycol as an internal standard.

EXAMPLE 2

The general process of Example 1 was followed in producing a number of products with varying mol ratios of reactants. Subexamples A–G are set forth in the following table.

From subexamples A through G below it is seen that both hydroxyl groups of GOAH can react with MA under these conditions, and the following two products are formed in varying ratios, depending on the conditions:

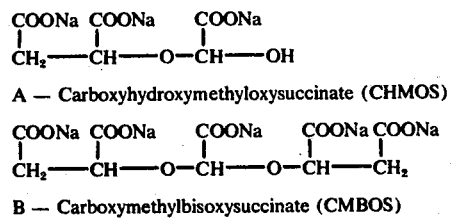

A — Carboxyhydroxymethyloxysuccinate (CHMOS)

B — Carboxymethylbisoxysuccinate (CMBOS)

In Example E, product B was formed as equal or greater than 94% by using a 3/1 mol ratio of MA to GOAH. Likewise, product A was formed as the predominant species in Example G by employing a 2/1 mol ratio of GOAH to MA.

| | Millimols MA GOAH | Mol Ratio MA/GOAH | Milliequivalents Acid Ca(OH)₂ Na₂CO₃ | | | Reflux Time, Hours | Mol Ratio, Converted MA Starting GOAH | Unconverted MA/FA Ratio | Comments |
|---|---|---|---|---|---|---|---|---|---|
| A | 20.4 10.0 | 2.04 | 50.8 | 73.0 | 80.0 | 2 | 0.67 | 95/5 | Products A & B both present |
| B | 20.4 10.0 | 2.04 | 50.8 | 73.0 | 80.0 | 6 | 1.04 | 66/34 | Products A & B both present |
| C | 20.4 10.0 | 2.04 | 50.8 | 73.0 | 80.0 | 16 | 1.41 | 17/83 | Products A & B both present |

-continued

|   | Millimols MA | Millimols GOAH | Mol Ratio MA/GOAH | Acid | Milliequivalents Ca(OH)$_2$ | Milliequivalents Na$_2$CO$_3$ | Reflux Time, Hours | Mol Ratio, Converted MA Starting GOAH | Unconverted MA/FA Ratio | Comments |
| --- | --- | --- | --- | --- | --- | --- | --- | --- | --- | --- |
| D | 20.4 | 10.0 | 2.04 | 50.8 | 73.0 | 80.0 | 64 | 1.45 | 0/100 | Products A & B both present |
| E | 30.6 | 10.0 | 3.06 | 81.2 | 83.2 | 90.0 | 16 | 1.94 | 31/69 | 94% B |
| F | 10.2 | 10.0 | 1.02 | 30.4 | 62.8 | 69.8 | 6 | 0.63 | 14/86 | Products A & B both present |
| G | 10.2 | 20.4 | 0.50 | 40.8 | 62.8 | 68.8 | 16 | 0.37 | 0/100 | 74 mol% yield of Prod. A based on starting MA |

Detergency of the compounds of the present invention is demonstrated by a miniature Terg-O-Tometer test. In this test the effectiveness of the detergents is measured by their ability to remove natural sebum soil from cotton cloth. By this method, small swatches of cloth, soiled by rubbing over face and neck, are washed with test solutions of detergents in a miniature laboratory washer. The washer employed is so constructed that two standard formulations and two test formulations can be used to wash different parts of the same soiled swatch. This arrangement ensures that all formulations are working on identical soil. The quantity of soil removed by this washing procedure is determined by measuring the reflectances of the new cloth, the soiled cloth, and the washed cloth, the results being expressed as percent soil removal. Because of variations in degree and type of soiling, in water and in cloth, and other unknown variables, the art has developed the method of using relative detergency ratings for comparing detergent effectiveness.

The relative detergency ratings are obtained by comparing and correlating the percent soil removal results from solutions containing the detergents being tested with the results from two defined control solutions. The two control solutions are selected to represent a detergent system exhibiting moderately high detersive characteristics (Control B) and a system exhibiting moderately low detersive characteristics (Control A). The systems are assigned detergency ratings of 5.0 and 3.0, respectively.

By washing portions of each soiled cloth with the control solutions, as well as with two test solutions, the results can be accurately correlated. The two control solutions are identical in formulation except for the builder, sodium tripolyphosphate being used in the higher control and sodium citrate in the lower control.

| Ingredient | Standard Solution Formulations Weight % |
| --- | --- |
| Linear alkylbenzene sulfonate (LAS) | 20 |
| Builder | 40 |
| Water | 8 |
| Sodium Sulfate | 24 |
| Sodium Silicate | 7 |
| Carboxymethylcellulose | 1 |

In each case the control solution is prepared by dissolving the appropriate formulation (1.5g) in one liter of 180-ppm hard water (calculated as ⅔ calcium carbonate and ⅓ magnesium carbonate). The tests were run at pH of 9.5. The pH was adjusted with NaOH. The relative detergency ratings were calculated by the following equation:

$$RD = 3.0 + 2.0 \frac{\%SR_{Test} - \%SR_{Control\ A}}{\%SR_{Control\ B} - \%SR_{Control\ A}}$$

The following table presents detergency data derived by the above-described test on detergency formulations containing LAS. Tests were performed with various modifications of the compound employed in 40% concentration in each formulation with LAS at 20 %. Also in the formulation were 1% carboxymethylcellulose, 7% sodium silicate, 8% water, and sufficient sodium sulfate to total 100%.

TABLE

Effect of CHMOS & CMBOS on Detergency of LAS Modified Miniature Terg-O-Tometer Test

| Test No. | Compounds Tested | Wt.% in Composition | RDR, 180-ppm water (0.15% Concentration) |
| --- | --- | --- | --- |
| 1 | LAS STP | 20 40 | 5.0 |
| 2 | LAS Na Citrate | 20 40 | 3.0 |
| 3 | LAS CHMOS | 20 40 | 4.2 |
| 4 | LAS CMBOS | 20 40 | 3.5 |
| 5 | LAS Na$_2$SO$_4$[1] | 20 40 | 0.6 |

[1]In addition to the 24% Na$_2$SO$_4$ usually present in the composition

These data show the effectiveness of the methoxysulfosuccinate compounds of this invention in increasing the detergency of detergent-active materials.

While the character of this invention has been described in detail with numerous examples, this has been done by way of illustration only and without limitation of the invention. It will be apparent to those skilled in the art that modifications and variations of the illustrative examples may be made in the practice of the invention within the scope of the following claims.

I claim:
1. Detergent-active materials of the formula

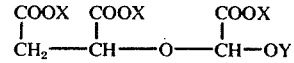

wherein Y is H or

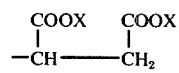

and X is H or a water-soluble salt-forming cation.
2. Compound of claim 1 in which Y is H.;
3. Compound of claim 1 in which Y is

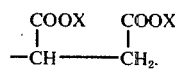

4. Compound of claim 1 in which X is alkali metal.
5. Compound of claim 1 in which X is H.

* * * * *